United States Patent
Zhdaneev et al.

(10) Patent No.: US 9,638,681 B2
(45) Date of Patent: May 2, 2017

(54) REAL-TIME COMPOSITIONAL ANALYSIS OF HYDROCARBON BASED FLUID SAMPLES

(75) Inventors: Oleg Zhdaneev, Bergen (NO); Christopher Harrison, Auburndale, MA (US); Youxiang Zuo, Edmonton (CA); Dingan Zhang, Edmonton (CA); William H. Steinecker, Farmersville, OH (US); Gordon R. Lambertus, Indianapolis, IN (US); Neil Bostrom, Watertown, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 1469 days.

(21) Appl. No.: 13/249,535

(22) Filed: Sep. 30, 2011

(65) Prior Publication Data

US 2013/0085674 A1    Apr. 4, 2013

(51) Int. Cl.
*E21B 49/08* (2006.01)
*E21B 49/10* (2006.01)
(Continued)

(52) U.S. Cl.
CPC ......... *G01N 33/2823* (2013.01); *E21B 49/10* (2013.01); *G01N 21/3504* (2013.01); *G01N 21/359* (2013.01); *G01N 21/3577* (2013.01); *G01N 21/643* (2013.01); *G01N 30/8658* (2013.01); *G01N 2030/8854* (2013.01)

(58) Field of Classification Search
USPC .................................. 702/6, 11, 12, 13, 50
See application file for complete search history.

(56) References Cited

U.S. PATENT DOCUMENTS

| 4,739,654 A | 4/1988 | Pilkington et al. |
| 5,166,747 A | 11/1992 | Schroeder et al. |

(Continued)

FOREIGN PATENT DOCUMENTS

| EP | 0508895 | 10/1992 |
| WO | 0173424 | 10/2001 |

OTHER PUBLICATIONS

Andrews et al., "Quantifying Contamination Using Color of Crude and Condensate", Oilfield Review Autumn 2001, pp. 24-43.*

(Continued)

*Primary Examiner* — Huan Tran

(57) ABSTRACT

Accurate, real-time formation fluids analysis can be accomplished using the systems and techniques described herein. A fluid analyzer includes a first mode of analysis, such as an optical analyzer, configured to determine a physical (optical) property of a fluid sample. The fluid analyzer also includes another mode of analysis, such as a composition analyzer, such as a gas chromatograph, configured to determine a component composition of the fluid sample. A data processor is configured to determine a quantity, such as a weight percentage, of a target component of the fluid sample in response results obtained from the first and second modes of analysis. Beneficially, the results are obtained at least in near real-time, allowing for interim results, such as results from the first analyzer to be used for one or more of tuning the compositional analyzer and for implementing quality control.

18 Claims, 9 Drawing Sheets

(51) Int. Cl.
*G01N 33/28* (2006.01)
*G01N 21/3504* (2014.01)
*G01N 30/86* (2006.01)
*G01N 21/359* (2014.01)
*G01N 21/64* (2006.01)
*G01N 21/3577* (2014.01)
*G01N 30/88* (2006.01)

(56) References Cited

U.S. PATENT DOCUMENTS

| | | | |
|---|---|---|---|
| 5,859,430 | A | 1/1999 | Mullins et al. |
| 6,993,979 | B2 | 2/2006 | Segeral |
| 7,095,012 | B2 * | 8/2006 | Fujisawa et al. ......... 250/269.1 |
| 7,384,453 | B2 | 6/2008 | Bostrom et al. |
| 7,637,151 | B2 * | 12/2009 | Raghuraman et al. .... 73/152.55 |
| 7,675,252 | B2 | 3/2010 | Chen et al. |
| 7,920,970 | B2 | 4/2011 | Zuo et al. |
| 8,013,295 | B2 | 9/2011 | Zhdaneev et al. |
| 8,250,904 | B2 | 8/2012 | Shah et al. |
| 2006/0226699 | A1 * | 10/2006 | Betancourt et al. ....... 303/113.2 |
| 2008/0141767 | A1 * | 6/2008 | Raghuraman et al. .... 73/152.55 |
| 2008/0173445 | A1 * | 7/2008 | Dong et al. ................ 166/264 |
| 2009/0158815 | A1 | 6/2009 | Shah et al. |
| 2009/0255672 | A1 | 10/2009 | Simpson et al. |
| 2010/0018287 | A1 | 1/2010 | Iakimov |
| 2010/0127163 | A1 | 5/2010 | Zhdaneev et al. |
| 2010/0162791 | A1 | 7/2010 | Breviere et al. |
| 2011/0061439 | A1 * | 3/2011 | Dong et al. .................... 73/1.03 |
| 2012/0053838 | A1 | 3/2012 | Andrews et al. |
| 2013/0151159 | A1 * | 6/2013 | Pomerantz et al. ............ 702/11 |
| 2013/0161502 | A1 * | 6/2013 | Pomerantz et al. .......... 250/255 |
| 2013/0293891 | A1 * | 11/2013 | Zazovsky et al. ............ 356/402 |

OTHER PUBLICATIONS

Betancourt et al., "Analyzing Hydrocarbons in the Borehole", Oilfield Review Autumn 2003, pp. 54-61.*

Extended Search Report of European Patent Application No. 12186377.3 dated Feb. 13, 2013: pp. 1-7.

Marshall et al., "Petroleomics: The Next Ground Challenge for Chemical Analysis," Accounts of Chemical Research, 2004, vol. 37(1): pp. 53-59.

Combined Search and Examination Report of British Application Serial No. 1206793.0 dated May 23, 2012.

* cited by examiner

REAL-TIME COMPOSITIONAL ANALYSIS OF HYDROCARBON BASED FLUID SAMPLES

BACKGROUND

1. Technical Field

This application relates generally to formation fluid analysis as may be accomplished downhole or at a surface. More particularly, this application relates to detection and identification of classes of interest within a formation fluid using a chromatography-based device.

2. Background Information

Downhole fluid analysis (DFA) is a rapidly growing discipline in wireline logging and has become a keystone in reservoir evaluation. DFA addresses the failed and overly optimistic assumption that oil reservoirs contain of "one giant tank of homogeneous hydrocarbon." Beneficially, DFA can be used to find compositional gradients as well as to identify compartments. Such analyses are typically based on bulk optical spectroscopy of samples of formation fluid to determine concentrations or ratios of components in sample fluid.

More recently, sophisticated optical measurement techniques have been developed to, among other things, determine methane ($C_1$), ethane-propane-butane-pentane ($C_2$-$C_5$), and heavier hydrocarbon molecule ($C_6^+$) compositions for hydrocarbons and gases. Current downhole analysis techniques, however, do not provide quantitative measurement of the individual hydrocarbon moieties for $C_2$, $C_3$, $C_4$, $C_5$ and molecules with more than six carbon atoms are indistinguishable.

Because different materials have different absorption characteristics, it becomes possible to make a determination as to what materials comprise the fluid sample, provided that the spectra of the materials which might be in the fluid sample are known. To that end, the spectra of water, gas, and several different oils are found in accordance to techniques generally well known in the art.

Using the absorption spectra of water, gas, crude and refined oils, and drilling fluids (lights), a least-squares analysis can be used to determine the components of the fluid sample. Alternatively or in addition a principal component analysis can also be used in a similar manner to determine the components of the fluid sample.

One such process referred to as "de-lumping" operates to determine compositional data from optical absorption spectra of samples of formation fluid in order to estimate molar distribution of the components in the component groups. Weight fractions for such components are then derived from molecular weights and the derived mole fractions.

For example, black oil de-lumping can be accomplished based on composition versus saturation pressure tables. Alternatively, de-lumping can be accomplished using tables of liquid and vapor compositions versus the liquid phase's gas/oil ratio ($R_s$) and/or the vapor phase gas/oil ratio ($R_v$) for the de-lumping process for greater accuracy. Unfortunately, processing the data in this manner requires substantial processing time. Consequently de-lumping precludes any compositional evaluations in real-time or even near real-time.

There are several approaches possible to make collected data quantitative and provide clients with information about the amount (weight or mole percentage) of the components of interests in the analyzable mixture:

In an absolute calibration method, a calibration plot is obtained in which the detector response versus the amount of the injected component could be utilized for quantification of the chromatogram or spectrogram. However, this method requires that conditions of the analysis during the calibration procedure and during the experiments are identical, which is a challenge for the variety of downhole conditions worldwide.

An internal standard method requires that some amount of the "standard" is carried together with the main module. During the analysis, the standard is mixed together with the formation fluid and injected into the separation module (e.g., chromatograph). This method requires bringing the "standard" downhole, mixing it with the sample of the formation mixture, identification of the "standard" response and its quantification, which is often very challenging.

In a case when it is difficult to resolve the added internal standard from other eluted peaks, a controlled admixture can be added to the second consequent chromatogram. Knowing the detector response factor, it is possible to quantify the amount of the analyzable component. Although this method is free of some of the problems of the internal standard method, it still requires bringing downhole the admixture that will be added.

A method of internal normalization assumes that all components elute from the column and are detected. The sum of the areas of all peaks represents 100% of the total concentration and the amount of the component of interest can be estimated from the proportion. However, in case of analysis of such a complex mixture as a crude oil, not all components will elute from the column (e.g., resins, asphaltenes, and very heavy saturates). Furthermore, integration and summation of all eluted peaks introduces significant error in the analysis results.

SUMMARY

Accurate, real-time analysis of fluids extracted from a subterranean formation is an ultimate goal for correct reservoir evaluation. Described herein are systems and techniques for implementing a combination of chromatography with another mode of analysis, such as optical techniques, for compositional analysis of formation fluids. The techniques can be accomplished within a wellbore, referred to herein as "downhole," at the surface, or some combination of downhole and surface environments, using multi-modal evaluation and analysis, such as of chromatography and spectrometry. The techniques can be applied to live oils, but are not meant to be limited to such applications. The combined chromatography and optical techniques, such as absorption spectroscopy, can be combined further with other techniques for mixture analysis.

In one aspect, at least one embodiment described herein provides a fluid analyzer for evaluating a fluid sample containing a reference component and at least one other component. The fluid analyzer includes an optical analyzer adapted to receive at least a portion the fluid sample. The optical analyzer is configured to determine an optical property of the fluid sample and to provide an optical analyzer output signal related to the determined optical property. The fluid analyzer also includes a composition analyzer, which is adapted to receive at least a portion of the fluid sample. The composition analyzer is configured to determine a component composition of the fluid sample and to provide a composition analyzer output signal indicative of the determined component composition. The fluid analyzer further includes a data processor in communication with each of the optical analyzer and the composition analyzer. The data processor is configured to determine a quantity of a target component of the at least one other components in response to receiving the optical analyzer output signal and the composition analyzer output signal.

In some embodiments, the data processor is configured to determine the quantity of the target component ($W_i^{GC}$) according to a predetermined algorithm. One such algorithm can be implemented according to the following relationship.

$$W_i^{GC}(\%) = \frac{A_i^{GC} \times R_i^{GC} \times W_{Ref}^{IFA}}{A_{Ref}^{GC} \times R_{Ref}^{GC}}$$

In the above equation, the value $W_i^{GC}$ refers to a quantity of target component; whereas, $A_i^{GC}$ refers to a target response area determined from composition analyzer output. The value $A_{ref}^{GC}$ refers to a reference response area determined from composition analyzer output; whereas, $W_{ref}^{FA}$ refers to a quantity of reference component determined from optical analyzer output signal. The value $R_i^{GC}$ refers to a composition analyzer detector response factor for the target component; whereas, $R_{ref}^{GC}$ refers to a composition analyzer detector response factor for the reference component.

In some embodiments, the optical analyzer includes an optical absorption spectrometer. The composition analyzer can also include one or more of a spectrographic analyzer and a chromatographic analyzer. In some embodiments, composition analyzer can be configurable in response to the optical analyzer output signal. Each of the optical analyzer and composition analyzer can also be adapted for use downhole, within a wellbore, such that the fluid sample is analyzed in situ.

In some embodiments, the fluid analyzer further includes a multiphase flowmeter adapted to receive at least a portion the fluid sample outside of a wellbore (e.g., at a surface) producing the fluid sample. At least one of the optical analyzer and composition analyzer may receive the fluid sample from the multiphase flowmeter.

In another aspect, at least one embodiment described herein provides a process for evaluating a fluid sample containing a reference component and at least one other component. The process includes receiving a fluid sample containing a reference component and at least one other component. An optical property of the fluid sample is determined. The reference component is quantified in response to the measured optical property. An independent composition evaluation of the fluid sample is also determined. The target component is quantified in response to the independent composition evaluation and the quantified reference component.

In some embodiments, determining the optical property of the fluid sample includes generating an optical absorption spectrogram of the fluid sample. Determining the independent composition evaluation can also include generating at least one of a chromatogram and a spectrogram of the fluid sample. In some embodiments, determining the independent composition evaluation further includes determining target and reference response areas in each of the at least one of the chromatogram and the spectrogram.

In some embodiments, quantifying the target component can be accomplished according to a predetermined algorithm. One such algorithm can be implemented according to the following relationship.

$$W_i^{GC}(\%) = \frac{A_i^{GC} \times R_i^{GC} \times W_{Ref}^{IFA}}{A_{Ref}^{GC} \times R_{Ref}^{GC}}$$

In the above equation, the value $W_i^{GC}$ refers to a quantity of target component; whereas, $A_i^{GC}$ refers to a target response area from determined the chromatogram/spectrogram. The value of $A_{ref}^{GC}$ refers to a reference response area from determined the chromatogram/spectrogram; whereas, $W_{ref}^{IFA}$ refers to a quantity of reference component determined from optical analyzer output signal. The value of $R_i^{GC}$ refers to a composition analyzer detector response factor for the target component; whereas, $R_{ref}^{GC}$ refers to a composition analyzer detector response factor for the reference component.

In some embodiments, the process further includes deriving from the determined optical property, one or more other properties, such as weight percentage of a $C_1$ component (e.g., $CH_4$); weight percentage of $C_2H_6$—$C_5H_{12}$ components, collectively; weight percentage of $C_6^+$ collectively; formation pressure (e.g., psig); formation temperature (e.g., degrees C.); gas-oil ratio; and condensate-gas ratio.

In some embodiments, more than one of the acts of receiving a fluid sample, determining an optical property, quantifying the reference, and determining an independent composition evaluation are accomplished downhole, within a wellbore. Alternatively or in addition, the fluid sample can be passed through a multiphase flowmeter, wherein the acts of receiving the fluid sample, determining an optical property, quantifying the reference, and determining an independent composition evaluation can be accomplished outside of a wellbore.

In some embodiments, further comprising pre-configuring a composition analyzer in response to the determined optical property of the fluid sample, the composition analyzer is adapted for determining the independent composition evaluation of the fluid sample. In some embodiments including comparing the determined optical property with the determined independent composition evaluation, an unfavorable comparison is indicative of a lack of quality in at least one of the determination of the optical property and the determination of the independent composition evaluation. In some embodiments, the process includes repeating the act of quantifying the target component for other targets of the at least one other components; and generating a summary report indicative of the quantified target components. In some embodiments, the act of quantifying comprises determining at least one of weight and mole fractions or percentages.

In yet another aspect, at least one embodiment described herein provides a fluid analyzer for evaluating a fluid sample containing a reference component and at least one other component. The fluid analyzer includes means for receiving a fluid sample containing a reference component and at least one other component; means for determining an optical property of the fluid sample; means for quantifying the reference component in response to the measured optical property; means for determining an independent composition evaluation of the fluid sample; and means for quantifying the target component in response to the independent composition evaluation and the quantified reference component.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DESCRIPTION OF THE PREFERRED EMBODIMENTS

Figure 1:
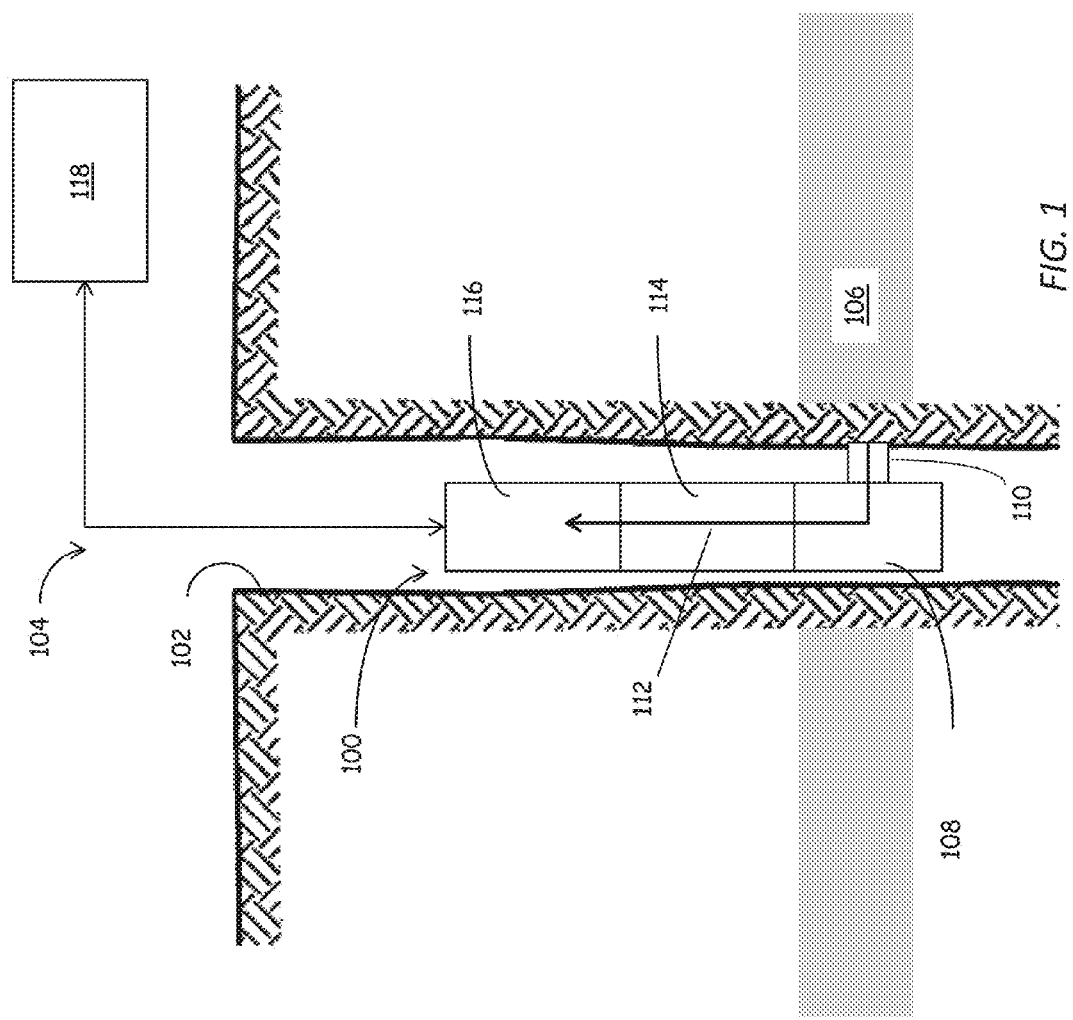
FIG. 1 shows, in partial cross section, one embodiment of a fluid analyzer deployed within a wellbore.

In the following detailed description of the preferred embodiments, reference is made to accompanying drawings, which form a part thereof, and within which are shown by way of illustration, specific embodiments, by which the invention may be practiced. It is to be understood that other embodiments may be utilized and structural changes may be made without departing from the scope of the invention.

The particulars shown herein are by way of example and for purposes of illustrative discussion of the embodiments of the present invention only and are presented in the case of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in that how the several forms of the present invention may be embodied in practice. Further, like reference numbers and designations in the various drawings indicate like elements.

The embodiments of processes described herein by way of illustrative example utilize optical analysis in combination with chromatographic and/or spectrometric measurement of a formation fluid sample to determine quantitative compositional analysis of the fluid sample. The combined techniques can also be used for one or more of calibration, quality control and analysis, and system performance tuning. Fluid analyzers, such as those described herein, can be controlled at least in part by operating software. Such software, for example, can include one or more algorithms to predict chromatographic/spectrometry response of an analyzable mixture.

Combination of optical and chromatographic measurements allows an in-situ quantitative identification of components of interest in a formation sample. Utilization of a gas chromatographic response prediction algorithm, for downhole GC system tuning, significantly improve system performance in a wide range of downhole conditions and analyzable oils. The proposed methodology and system designs can complement the existing optical/chromatographic methods and future analytical characterization apparatuses.

According to the techniques described herein, significant improvements in real-time formation fluids characterization at downhole conditions can be achieved in various applications. For example, the techniques described herein can be implemented on different platforms (e.g., wireline, logging while drilling, testing,) utilizing different types of conveyance (e.g., wireline cable, drilling tubing, coil tubing, tractor). The techniques described herein offer improvement over conventional methods of chromatography and spectrometry that require either internal or external standards carried with the chromatographic and/or spectrometric system and are not able to provide automatic system tuning to optimize analysis of a given unknown mixture.

FIG. 1 shows an embodiment of a downhole sampling tool 100 being deployed within a wellbore 102. The tool 100 can be deployed, for example, from a wire line truck (not shown). A wireline cable 104 is deployed into well 102. The downhole sampling tool 100 is disposed at the end of the cable 104, shown lowered in a vicinity of a subterranean formation 106. According to some embodiments, the downhole sampling tool 100 performs focused fluid extraction using a sampling module 108 having a flowline extraction probe 110. For example, a formation fluid extraction tool 108, such as the focused fluid extraction tool known as a Quicksilver Probe, available in the commercial services provided by Schlumberger Technology Corporation, Sugar Land, Tex., USA. The Quicksilver Probe fluid sampling tool 108 is part of the Modular Formation Dynamics Tester (MDT) tool suite, also available in the commercial services provided by Schlumberger. The sampling tool 108 includes a fluid extraction probe 110 adapted to obtain a sample of fluids from the subterranean formation 106. In at least some embodiments, the extraction probe 110 includes filters for filtering out at least particulate matter from fluid samples. The sampling tool 108 directs at least a portion of extracted formation fluid into a flowline 112.

In some embodiments, the tool 100 also includes a downhole fluid analysis module 114, such as an optical analysis module adapted to receive at least a portion of the fluid sample. The optical analyzer can be configured to determine an optical property of the fluid sample and to provide an output signal related to or otherwise indicative of the optical property. An example of such an optical analyzer is the Composition Fluid Analyzer (CFA) module of the MDT tool suite. The optical analysis module 114 is configured to perform near-infrared optical absorption spectrometry and fluorescence emission measurements for analyzing fluids as they flow through the tool 100. The optical analysis module 114 can be used to determine gas-fraction concentrations and to identify fluid types, respectively, as fluids flow through the optical analysis module 114.

In particular, a single-phase reservoir gas flowing through the optical analysis module 114 is analyzed using near-infrared optical absorption spectrometry to determine in real time the concentration of one or more of: (i) methane ($C_1$); (ii) ethane-propane-butane-pentane ($C_2$-$C_5$); and (iii) heavier hydrocarbon molecules ($C_6^+$). An example of such an analyzer is described in U.S. Pat. No. 7,637,151, entitled "Enhanced Downhole Fluid Analysis," assigned to Schlumberger Technology Corporation and incorporated herein by reference in its entirety.

In at least some embodiments, the tool 100 includes a second fluid analysis module 116. For example, the second fluid analysis module can include a composition analyzer, such as a downhole gas chromatography module 116. The composition analyzer is configured to determine a component composition of the fluid sample and to provide an output signal indicative of the determined composition. For the example embodiment using gas chromatography, the gas chromatography module 116 is configured to obtain a chromatogram of sampled formation fluids available within the flowline 112 portion of the tool 100. An example of such a device is described in U.S. Pub. App. No. 2010/0018287, entitled "Wireline Downhole Gas Chromatograph and Downhole Gas Chromatography Method," and U.S. Pat. No. 7,384,453, entitled "Self Contained Chromatography System," each assigned to Schlumberger Technology Corporation and incorporated herein by reference in its entirety.

According to some embodiments, data from the tool 100 can be recorded and/or processed downhole within tool 100, and/or can be transmitted to a surface location, such as the wireline truck, for recording and/or processing. The wireline 104 can be configured to provide telemetry between the downhole tool 100 and the surface equipment, such as a data processing system 118. The tool 100 can be controlled locally with processing systems provided within tool 100 itself, and/or from the surface using the processing systems 118.

The processing system 118 can be located in the wire line truck, at location near the wellbore 102 or at a remote location. According to some embodiments, some or all of the functionality of processing system 118 can be located within sampling tool 100. The processing system 118 can be used to control, record and/or process data from one or more modules 112, 116 of the sampling tool 100. The processing system 118 can include one or more central processing units, storage system, communications and input/output modules, a user display and a user input system. Input/output modules include modules to communicate with and control sampling tool 100.

In at least some embodiments, the data processing system 118 is in communication with each of the optical analysis module 114 and the gas chromatography module 116. The data processor 118 is configured to determine a quantity of a target component of the various components within the fluid sample in response to receiving an output signal from the optical analysis module 114 and an output signal from the gas chromatograph module 116. The processing system 118 can be configured to execute one or more processes according to preprogrammed instructions stored within memory and available to the processor 118. In some embodiments, the data processing system 118 can include a signal analyzer. One or more of the processing steps described herein can be implemented within the data processing system 118, which may include one or more of a general purpose computer, a specific programmed processor, hardware (e.g., elements configured to implement digital signal processing), firmware, and combinations of such devices.

The data processing system 118 can be configured to combine results from both the optical analysis module 114 and the gas chromatography module 116 to obtain quantitative computational analysis for a formation fluid sample. Beneficially, such results can be obtained without requiring an internal standard. The ability to obtain such quantitative results without requiring the added weight, size and complexity of the internal standard is highly desirable for downhole analysis as is achievable with the devices and techniques described herein.

Figure 2:
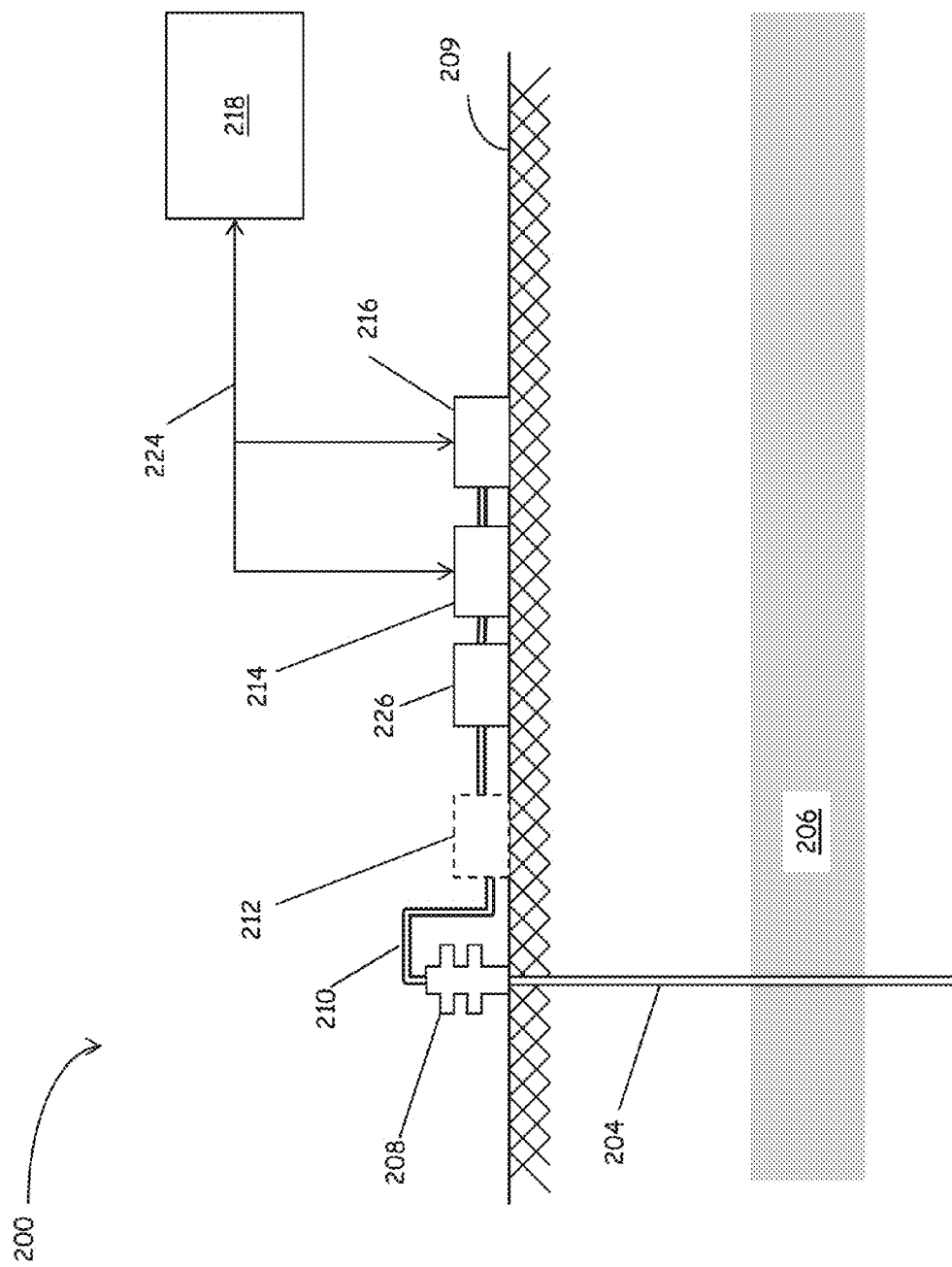
FIG. 2 shows, another embodiment of a fluid analyzer deployed near a surface of a wellbore.

Referring next to FIG. 2, an alternative embodiment of a sampling system 200 deployed along a surface terrain that may be land-based or along a sea floor. In such configurations, the tool can be employed to sample formation fluids after they have been extracted from a subterranean formation 206 and transported by tubing 204 to the surface 209. Such testing can be used after well completion, for example during a production phase. The illustrated system 200 is employed for a completed well having in place tubing 204 in fluid communication with a subterranean formation 206. The tubing 204 conveys extracted hydrocarbon to a surface through any of various well known techniques for extraction or pumping. The extracted fluids flow through a wellhead completion 208. The well completion 208 can include one or more elements, as commonly employed in such applications, such as blow-out preventers, and valve networks otherwise known as "Christmas trees."

The sampled formation fluids extracted from the well are channeled at the surface (including subsea surfaces) through a flowline 210, for example, to production facilities for transporting extracted hydrocarbons from the oilfield to market. In some embodiments, a bypass manifold 212 (shown in phantom) can be provided to separate a manageable sample of high-volume formation fluids flowing through the flowline 210 for analysis without otherwise impacting production of the well.

A relatively small sample can serve as a basis for evaluation of the extracted formation fluids. In the illustrative embodiments, the system 200 includes a fluid analysis module 214, as may function similar to the Composition Fluid Analyzer (CFA) module 114 of FIG. 1, but need not be confined by downhole requirements as in the previous example. In at least some embodiments, the fluid analysis module 214 includes an optical absorption spectrometer, for example, configured to perform near-infrared optical absorption spectrometry and in at least some embodiments, fluorescence emission measurements for analyzing fluids as they flow through the system 200. As with the downhole tool 100 (FIG. 1), the fluid analysis module 214 can be used to determine gas-fraction concentrations and to identify fluid types, respectively, as fluids flow through the fluid analysis module 214. Thus, the fluid analysis module 214 can be used to determine in real time the concentration of one or more of: (i) methane ($C_1$); (ii) ethane-propane-butane-pentane ($C_2$-$C_5$); and (iii) heavier hydrocarbon molecules ($C_6^+$).

In at least some embodiments, the system 200 includes a second fluid analysis module 216, such as a composition analyzer 216. For example, the second fluid analysis module 316 can include a gas chromatography module 216. The gas chromatography module 216 is configured to obtain a chromatogram of sampled formation fluids obtained from the flowline 210 portion of the system 200. The gas chromatography module 216 can include a volumetric chamber (e.g., piston chamber) to reduce the volume of a portion of the sampled formation fluids, thereby reducing the sampled formation fluid pressure to promote gaseous phase in support of gas chromatographic analysis.

Each of the first and second fluid analyzer modules 214, 216 provides respective output signals indicative of its respected detected physical properties of the fluid sample being analyzed. In at least some embodiments, output signals from one or more of the fluid analyzer modules 214, 216 are provided to a data processing system 218.

The data processing system 218 can be located at a surface location, for example, at location near the wellbore 102 or at another remote location. For example, in subsea surface configurations, the processing system 218 may be located on a sea surface rig, such as a vessel. Any suitable means of communication between the tool 200 and the processing system 218, such as telemetry 224, can be provided to establish communications between the one or more fluid analyzer modules 214, 216 and the data processing system 218. Communication can be bidirectional, for example, transporting analyzer output signals in one direction to the data processing system 218 and in another direction, sending control signals to one or more of the analyzers.

In at least some embodiments, the data processing system 218 is configured to determine a quantity of a target component of the various components within the fluid sample in response to receiving an output signal from the optical analyzer and an output signal from the computational analyzer. The data processing system 218 can be configured to execute one or more processes according to preprogrammed instructions stored within memory and available to the data processing system 218.

Once again, the data processing system 118 can be configured to combine results from both the optical analysis module 214 and the gas chromatography module 216 to obtain quantitative computational analysis for a formation fluid sample. Beneficially, such results can be obtained without requiring an internal standard. The ability to obtain such quantitative results without requiring the added weight, size and complexity of the internal standard is highly desirable for downhole analysis and is achievable with the devices and techniques described herein.

In some embodiments, the system 200 includes a multiphase sampler 226. A multiphase sampler 226 is in fluid communication with the flowline 210 and is configured to capture samples of multiphase fluids at line conditions, directly from the flowline, while maintaining thermodynamic equilibrium, thereby preserving accurate flowline pressure and temperature conditions. Such sampling allows collected fluid samples to be analyzed onsite. Sampling fluids from the flowline in this manner preserves gas-oil ratios and compositional integrity of the fluid sample.

An example of a multiphase sampler 226 is described in U.S. Pat. No. 6,993,979, assigned to Schlumberger Technology Corporation and incorporated herein by reference in its entirety. The example device includes a multiphase mass flow meter with variable venturi nozzle. A sample of fluids can be obtained within the proximity of the venturi throat of the multiphase sampler 226. In at least some embodiments both the optical absorption measurements and the gas chromatography measurements are obtained from the formation fluid stream close to the venturi throat of the multiphase sampler 226. For example, one or more of the optical analyzer and the gas chromatography module can be incorporated within the multiphase sampler 226.

In a surface embodiment, the analysis process can include one or more manual steps. For example a technician can manually perform a sampling of the composition evaluation by means of a compositional analyzer, such as the gas chromatography module 216. Optical measurements can be obtained from an optical analyzer 214 that can be brought into contact with a flowing stream of hydrocarbons obtained from the well.

Figure 3:
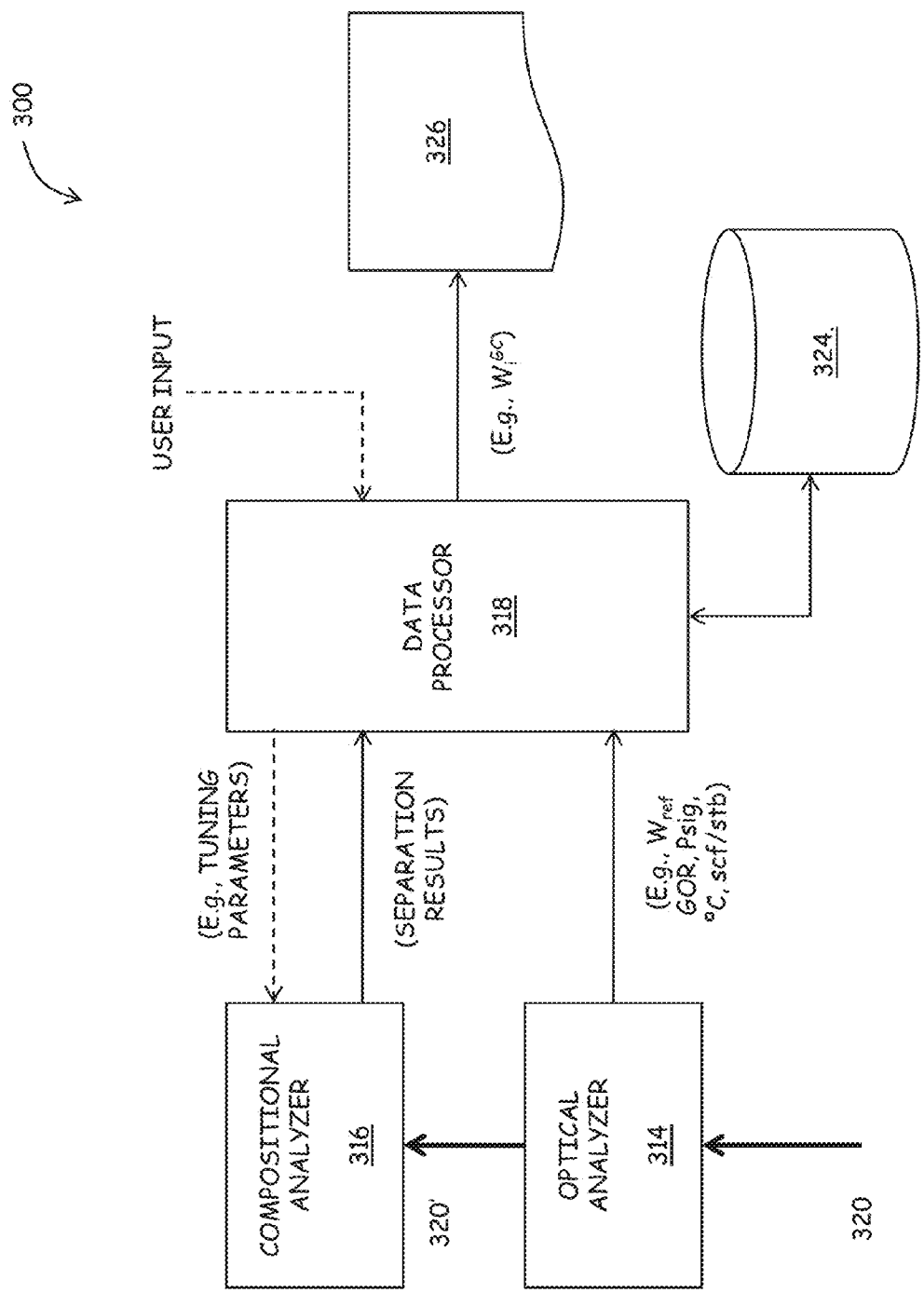
FIG. 3 shows a functional block diagram of an embodiment of a fluid analyzer.

Referring next to FIG. 3, a functional block diagram of an embodiment of a fluid analysis system 300 is shown in more detail. The system 300 includes an optical analyzer 314, a compositional analyzer 316 and a data processor 318. The optical analyzer receives a fluid sample 320. In the example embodiments described herein, the fluid samples are hydrocarbon based, but otherwise compositionally unknown at the time of sampling.

In some embodiments, the optical analyzer 314 contains an optical absorption spectrometer. Absorption spectra, for example, in the visible to near infrared region can be used to make low-resolution compositional analysis of a sample of fluids. One or more of visible and near infrared light to quantify a fluids composition as it flows through the analyzer 314. A spectrum of light is transmitted through the fluid to an array of detectors tuned to selected wavelengths. The amount of light absorbed by the fluid depends on its composition. The measured absorption spectrum is represented as a linear combination of unique absorption spectra, such as spectra for $C_1$, $C_2$-$C_5$, $C_6^+$, $CO_2$ and $H_2O$, allowing determination of the weight percent of each molecular group. One example of an optical analyzer 314 is the CFA module introduced above.

In another variant, the optical analyzer 314 is a live fluid analyzer (LFA) module of the MDT tool suite that incorporates an absorption spectrometer to quantify the amount of reservoir and drilling fluids in the sample. The optical sensor in the LFA module uses this principle to measure the absorption of light at multiple wavelengths, e.g., 1670 nm and 1720 nm.

The optical module 314 provides an output signal indicative of measured and/or calculated results determined from analysis of the sampled fluid 320. For example, the output can contain one or more of a weight of a reference component $W_{ref}$, e.g., $C_1$, an indication of a gas-oil ratio (e.g., scf/stb), and other information, such as pressure and temperature information (e.g., Psig, ° C.). To that end, the optical analyzer 314 can include other sensors, for example, sensing one or more of pressure and temperature of one or more of the fluid sample and a local environment. Example of output data from an optical module 314 are provided in Table 1.

TABLE 1

Output data from downhole optical fluid analysis module.

| | |
|---|---|
| $CH_4$ (i.e., $C_1$) | weight % |
| $C_2H_6$—$C_5H_{12}$ (i.e., $C_2$—$C_5$) | weight % |
| $C_6+$ | weight % |
| Formation pressure | psig |
| Formation temperature | ° C. |
| Gas/Oil ratio (GOR) | scf/stb |

In some embodiments, the compositional analyzer 316 is configured to obtain a chromatogram of the sampled formation fluids. The compositional analyzer 316 can be a mass sensitive chromatographic detector (e.g., helium ionization detector for gas chromatography). An example of gas chromatography techniques currently adapted for formation fluid analysis is described in U.S. Pat. No. 7,384,453, assigned to Schlumberger Technology Corporation and incorporated herein by reference in its entirety. During evaluation of a formation of hydrocarbons, at least a portion of sampled formation fluids can be stored in a sampling chamber. The sample can be subjected to a volumetric change, for example, to separate dissolved gas and liquid hydrocarbon phases. In some embodiments, any water, that may be present in the collective liquid hydrocarbon (oil) case, can be separated. The gas chromatography module 116 in a separate mode of analysis provides an output that is indicative of individual carbon components within the fluid sample.

Utilizing gas chromatography measurements, it is possible to distinguish between the components in the formation mixture and to separate and identify them with an appropriate detector. Examples of such detectors are provided in co-pending U.S. patent application Ser. No. 12/872,452, entitled "Downhole Sample Analysis Method," and U.S. Pat. Pub. No. 2010/0127163, each assigned to Schlumberger Technology Corporation and incorporated herein by reference in its entirety.

In operation of the gas chromatography system 316, standard analytical protocols that include column type and configurations, temperature programs, carrier gas flow rates and pressures, injector and detector temperatures are used for characterization. In some embodiments, more than one chromatographic system and protocol can be used for analysis of gas and liquid hydrocarbon phase fractions to maximize resolution and accuracy.

The data processor 318 receives output data provided by each of the optical analyzer 314 and the compositional analyzer 316. The data processor 318 is configured to determine a quantity of a target component 326 of the various components within the fluid sample in response to the received data. In at least some embodiments, the data processor 318 calculates a weight percentage of the target component $W_i$ according to the following expression:

$$W_i^{GC}(\%) = \frac{A_i^{GC} \times R_i^{GC} \times W_{Ref}^{IFA}}{A_{Ref}^{GC} \times R_{Ref}^{GC}}$$

The term $A_i$ represents a response area of target component i obtainable from output of the gas chromatograph. The term $A_{ref}$ represents the response area of a reference component (e.g., $CH_4$), similarly obtainable from output of the gas chromatograph 316. The term Wref is the weight percent of the reference component (wt. % of total) obtained from the optical analyzer 314. The term Wi is the weight percent of target component i, and R is the detector response factor (which may include molecular weight and/or carbon number corrections if necessary). The superscripts "GC" and "IFA" indicate whether the values used in evaluating the expression are obtained from the compositional analyzer 316 (e.g., by gas chromatography—GC) or from the optical analyzer (e.g., by injection flow analysis—IFA). Application of the above expression provides a simple and effective way to quantify/calibrate the chromatographic/spectrometry results.

In at least some embodiments, the system 300 includes a memory device 324 to, for example, store results that can be used in supporting evaluation of the above expression. For example, the memory device 324 can provide a pressure, volume, temperature (PVT) database storing one or more of weight percentage, molecular weight, mole percentage, specific gravity of single carbon number components ($CO_2$, $C_1$, $C_2 \ldots C_{30}^+$).

Figure 4:
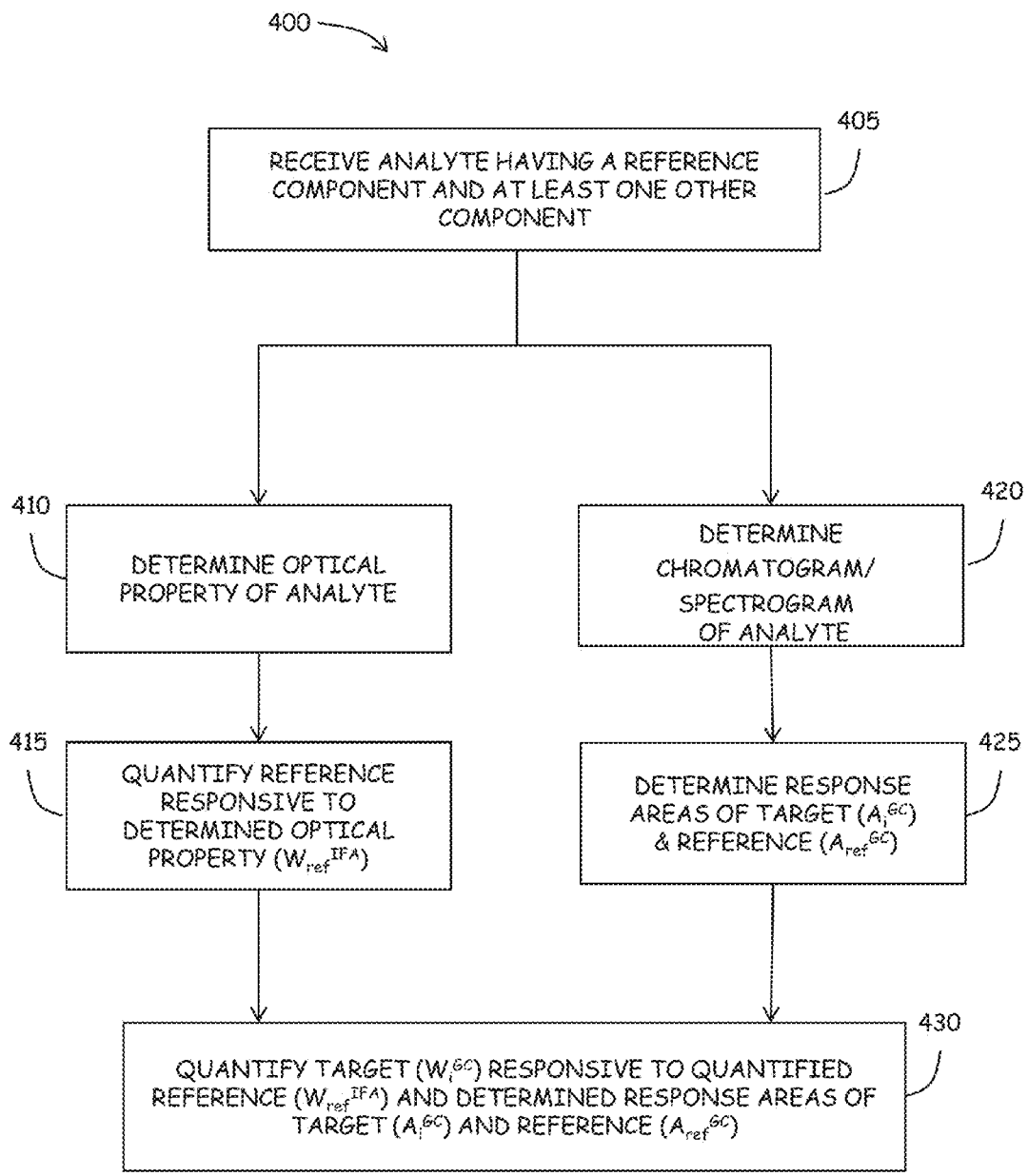
FIG. 4 shows a flow diagram of an embodiment of a process for analyzing a fluid sample, in which a target component within the fluid sample is quantified.

FIG. 4 shows a flow diagram of an embodiment of a process 400 for analyzing a fluid sample, in which a target component within the fluid sample is quantified. In particular, the process can be used for quantifying a component in an analyzable mixture as described below. A small quantity of a formation fluid, which is removed from a reservoir, is received, for example, through a flowline, at 405. A composition of the formation fluid includes a reference component (e.g., $C_1$) and at least one other component (e.g., $C_2^+$).

In at least some embodiments, the received fluid sample is filtered, for example, to remove sand particles.

A physical property of the fluid sample, such as an optical property, is determined at 410. In particular, the optical property can be indicative of one or more of the reference component and the target component. In determining the optical property, the fluid sample can be delivered to the optical module 114, 214, 314 for example, via a flowline within a sampling tool 100. In at least some embodiments, the optical property can be used to determine a weight percentage of the reference component $W_{ref}^{IFA}$ 415. It is understood that in at least some embodiments, the sampled fluid can be mixed with a reagent to facilitate optical identification of a target component (analyte), such as the reference component. Such techniques can include one or more of continuous flow, in which the reagent and sampled fluid are mixed until an equilibrium response is achieved, titration and injection flow analysis.

Another compositional analysis of the fluid sample is performed at 420. For example, the compositional analysis can include chromatography, such as gas chromatography to determine a chromatogram of the sample, including indications of the reference and target components. At least a portion of the fluid sample is delivered to the compositional analyzer, for example, including a gas chromatograph. An output of the compositional analyzer can include a chromatogram of the sampled fluid, including chromatographic results of the reference component and at least one other component, including the target component. Such chromatographic results can include a curve having peak responses indicative of certain components.

In more detail, the liquid or gas is allowed to expand and evaporate in a sample chamber, such as the manner described within U.S. Pat. No. 7,920,970, assigned to Schlumberger Technology Corporation and incorporated herein by reference in its entirety. After expansion, a valve injects the evaporated mixture into the chromatographic column where, due to difference in the affinity to the stationary phase deposited e.g., on the column's walls, separation between the components of interest is achieved. The separated components elute into a detector for detection.

Without a priori knowledge of a hydrocarbon sample, one would have to go with a standard protocol. For example, a standard protocol would be used irrespective of whether the sample is a dry gas, with components predominantly to $C_7$, or a black oil, with components all the way to $C_{36}$ and higher. Beneficially, evaluation results of the fluid sample obtained by the optical analyzer 114 can be used for tuning and otherwise optimizing gas chromatography to improve resolution and accuracy. Without the possibility of tuning, analysis according to such standard protocols would result in unnecessarily longer analysis times. Long wait times for analysis during logging, for example, not only translate to higher costs for services, but also increase the risk of tools sticking within the well bore. Longer analysis times also result in an increased use of consumables such as carrier gas, which is a particularly important consideration in a downhole environment, as only limited supplies exist.

An area under a curve of the chromatogram associated with each respective component, such as the reference and target component can be determined. For example, an output of the gas chromatograph 116, 216, 316 indicative of a chromatogram of the fluid sample can be passed to a data processor 118, 218, 318 for processing. Processing can include identification of one or more peaks indicative of a reference component, a target component, and other components present within the fluid sample at 425. Alternatively or in addition, processing can include determining an area under a curve of the chromatogram associated with one or more peaks, e.g., $A_i^{GC}$ $A_{ref}^{GC}$.

An output signal from the optical analyzer (e.g., weight percent of the reference component, e.g., $C_1$) and from the compositional analyzer (e.g., chromatograms, from which areas under chromatographic peaks that correspond to the components of interest can be determined, including the reference component, e.g., $C_1$) is delivered to the data processing system. The target component is quantified, for example, according to its weight percentage $W_i$ at 430. Quantification of the target component is responsive to signals received from the optical analyzer $W_{ref}^{IFA}$ and compositional analyzer, $A_i^{GC}$, $A_{ref}^{GC}$ according to a predetermined relationship. One such relationship is described above, in relation to FIG. 3. Application of the equation, substituting in known quantities of $W_{ref}^{IFA}$, $A_i^{GC}$, $A_{ref}^{GC}$ along with response factors for the gas chromatograph at each of the reference component $R_{ref}^{GC}$ and target component $R_i^{GC}$, results in quantification of the a weight percentage $W_i$ of the target component without requiring any internal standard. In at least some embodiments, the acquired chemical information can be presented in a final report characterizing the formation mixture.

Figure 5:
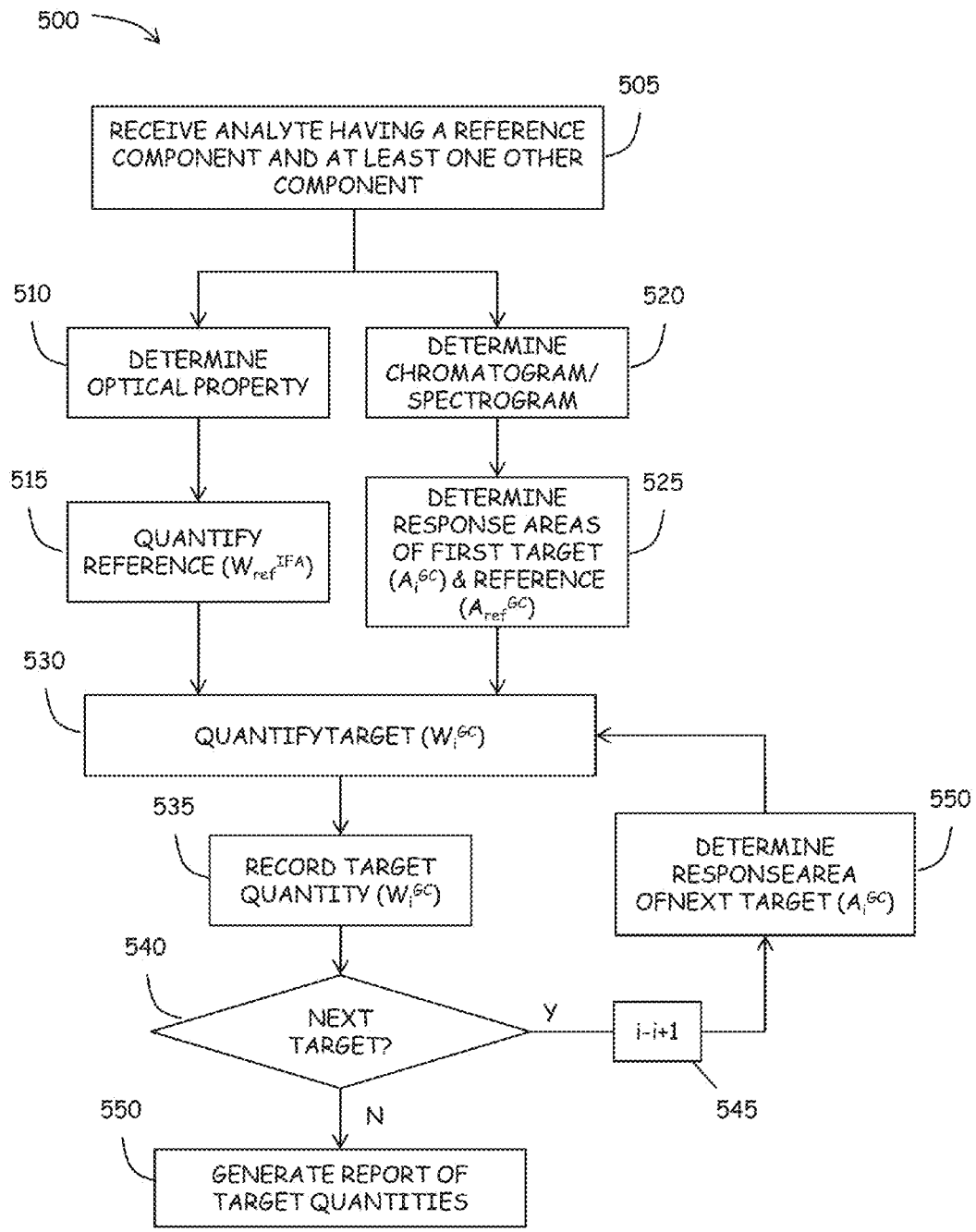
FIG. 5 shows a flow diagram of another embodiment of a process for analyzing a fluid sample, in which multiple target components within the fluid sample are quantified and recorded.

FIG. 5 shows a flow diagram of another embodiment of a process 500 for analyzing a fluid sample, in which multiple target components within the fluid sample are quantified and recorded. The process 500 can be used to quantify one or more than one targets of an individual fluid sample, for example, by repeating the process 400 described above in reference to FIG. 4.

An analyte having a reference component and at least one other component at is received at 505. An optical property of the fluid sample is determined at 510. A reference component of the fluid sample is quantified $W_{ref}^{IFA}$ at 515. A chromatogram is determined at 520. Response areas of first target $A_i^{GC}$ and reference $A_{ref}^{GC}$ are determined at 525. A first target it quantified $W_i^{GC}$ at 530. The quantity of the first target is recorded at 535.

Whether the process should be repeated for additional targets is determined at 540. For example, a predetermined list of target components can be provided or otherwise identified. To the extent the process is repeated, an indexing variable i can be incremented at 545, and a response area of the next target $A_{i+1}^{GC}$ in the predetermined list of targets is determined at 550. A quantity of the next target $W_{i+1}^{GC}$ is determined at 530, applying the same expression, updated according to the next target $A_{i+j}^{GC}$ and also using an appropriate detector response factor for the next target $R_{i+j}^{GC}$. The results for the next target $W_{i+1}$ are recorded at 535, and the process repeated until no further targets remain. At that time, the results can be generated, for example, in a report at 550.

Figure 6:
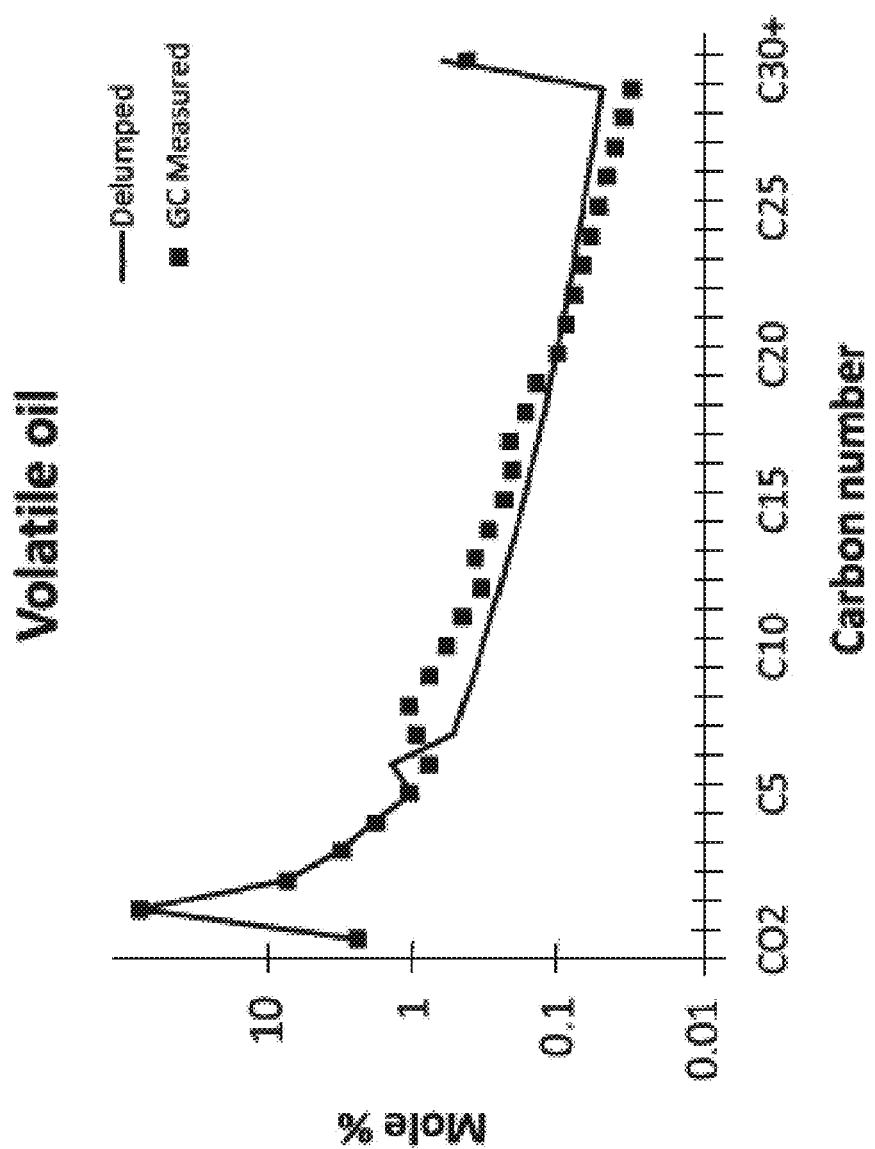
FIG. 6 shows a logarithmic plot of analysis results of a fluid sample obtained from one embodiment of a fluid analyzer, also showing results for the same fluid sample using obtained de-lumping analysis.

So-called de-lumping techniques can be used to characterize the $C_3$, $C_5$ (or $C_2$-$C_5$) and $C_6^+$ fractions obtained from an optical fluid analysis module. Such techniques are described in U.S. Pub. Pat. App. No. 2009/0158815 assigned to Schlumberger Technology Corporation and incorporated herein by reference in its entirety. De-lumping techniques are based on a database that was collected during many years of samples analysis from many locations and reservoirs. The techniques described herein, whether accomplished downhole or at a surface, combine optical analyzer results with gas chromatographic module for in-situ fluid analysis allowing real-time or at least near real-time results. An ability to obtain real-time results allows for an opportunity for other process improvements, such as quality control and hardware tuning of the gas chromatography system, for example, to obtain better resolution between the components of interest within short period of time. FIG. 6 shows a logarithmic plot of analysis results of a fluid sample obtained from one embodiment of a fluid analyzer, also showing good agreement compared to results for the same fluid sample obtained using de-lumping analysis.

As described above in this document the chromatographic module utilizes as an input results obtained from the optical module (e.g., weight % of $C_1$, $C_2$-$C_5$, $C_6$), temperature of the reservoir, and the density of the analyzable mixture. These parameters can be entered manually by operator or read from the specified file generated automatically based on the data from optics module and transferred to the logging cabin by telemetry system. The program as an output provides the predicted composition of the analyzable mixture in terms of carbon number weight % in the range $C_1$-$C_{36}^+$, and the weight percent of the concomitant gases ($N_2$, $CO_2$). The example of de-lumping results that was compared with laboratory measurements is presented on the FIG. 6. More than 100 different fluid samples were tested. The agreement between the de-lumped and GC data is good (accuracy for GOR is 5-6%, for density—3-4%, viscosity—10-20%) for different types of reservoir fluids.

Figure 7:
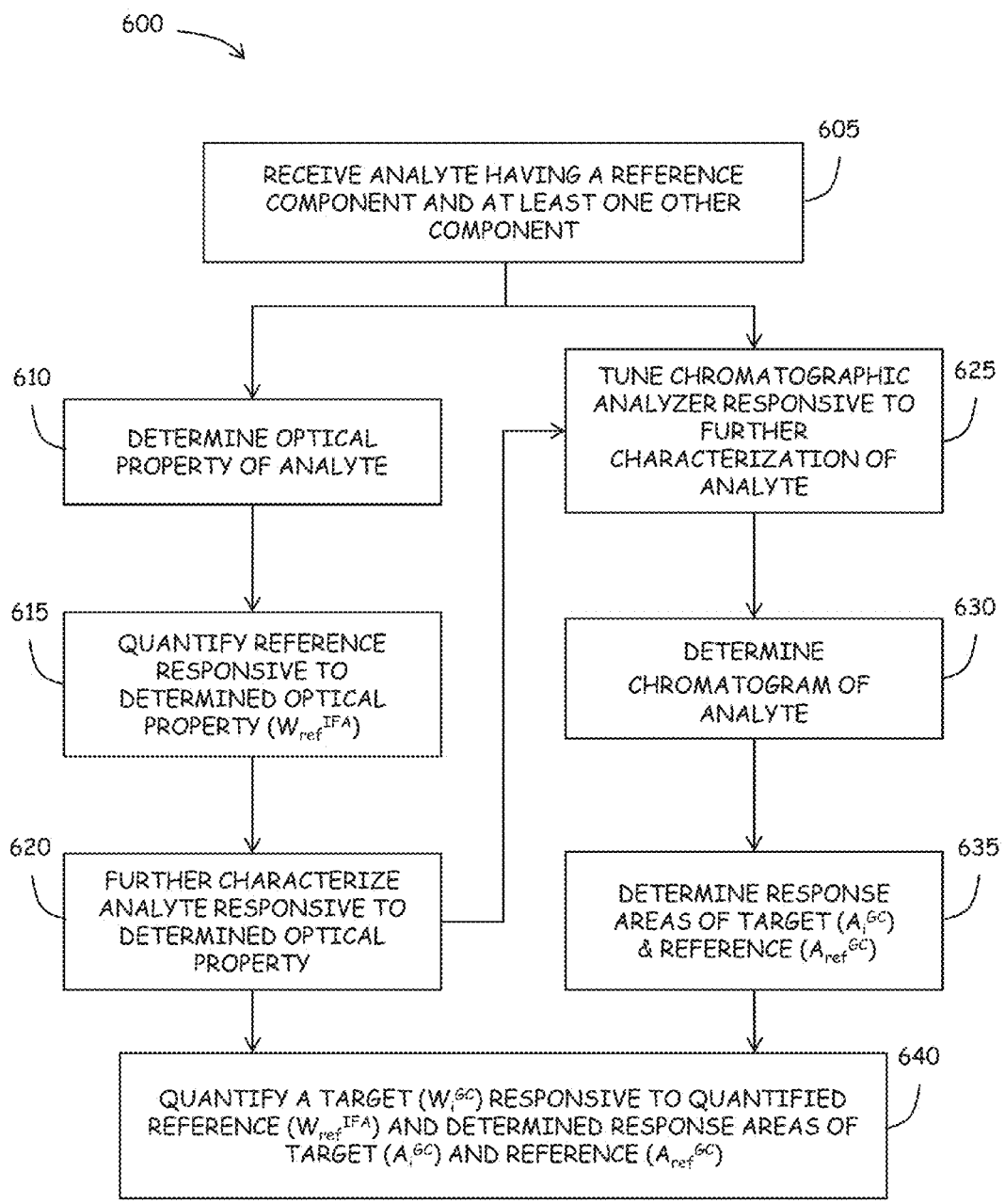
FIG. 7 shows a flow diagram of an embodiment of a process for analyzing a fluid sample, in which optical properties obtained from the fluid sample are used for chromatograph tuning for obtaining further analysis results of the fluid sample.

In at least some embodiments, results obtained by one or more elements of the fluid analysis system can be used to achieve a gas chromatography response forecasting. For example, results or at least interim results of one or more elements of the fluid analysis system can be used to adjust hardware of the gas chromatography system (e.g., selection of the most suitable column/columns to perform the analysis). FIG. 7 shows a flow diagram of an embodiment of a process for analyzing a fluid sample, in which optical properties obtained from the fluid sample are used for chromatograph tuning for obtaining further analysis results of the fluid sample.

An analyte having a reference component and at least one other component is received at 605. One or more optical properties of the analyte are determined at 610. The reference component is quantified responsive to the determined optical property $W_{ref}^{IFA}$ at 615. The analyte is further characterized at 620 responsive to the one or more determined optical properties.

Having characterized the analyte in real time, or at least near real time, allows the chromatographic analyzer to be tuned at 625 responsive to further characterization of the analyte. The results from the optical analyzer can serve as a predictive indicator as to the composition of the fluid sample. A chromatogram of the analyte is determined at 630. Response areas under the respective peaks of the chromatogram are determined at 635 for the target component $A_i^{GC}$ and one or more reference components $A_{ref}^{GC}$. The target $W_i^{GC}$ is quantified at 640 responsive to quantified reference $W_{ref}^{IFA}$ and the determined response areas of target $A_i^{GC}$ and reference $A_{ref}^{GC}$.

Figure 8:
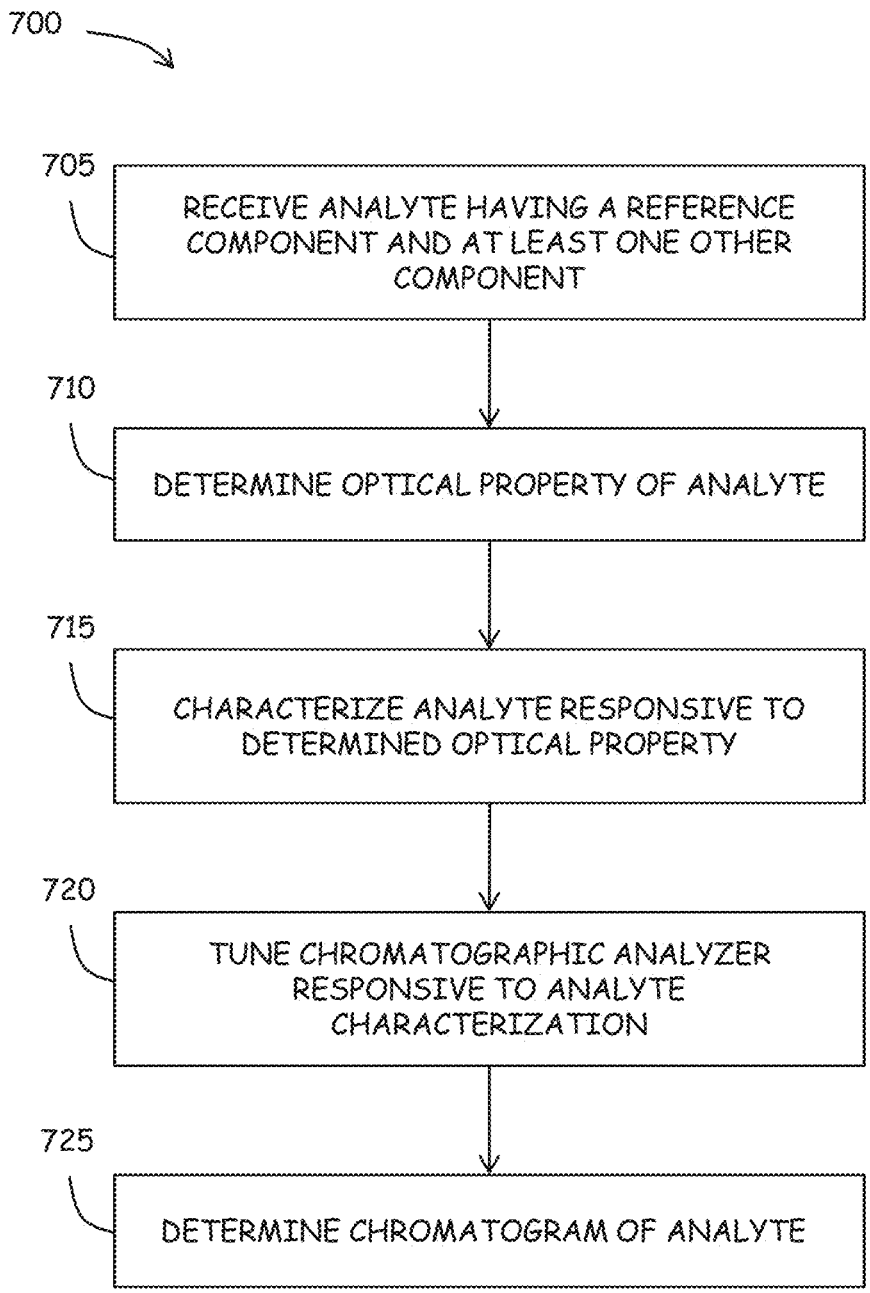
FIG. 8 shows a flow diagram of another embodiment of a process for analyzing a fluid sample, in which optical properties obtained from the fluid sample are used for chromatograph tuning for obtaining further analysis results of the fluid sample.

In an alternative embodiment illustrated in the flow chart of FIG. 8, an example process 700 is identified for analyzing a fluid sample using optical analysis and gas chromatographic analysis, in which a gas chromatograph is tuned in response to optical properties obtained from the fluid sample. In particular, an analyte (e.g., sample fluid) having a reference component and at least one other component is received at 705. An optical property of analyte is determined at 710. The analyte is characterized at 715 responsive to the determined optical property. The chromatographic analyzer is tuned at 720 responsive to analyte characterization. A chromatogram of analyte is determined at 725 after having tuned the chromatographic analyzer.

Figure 9:
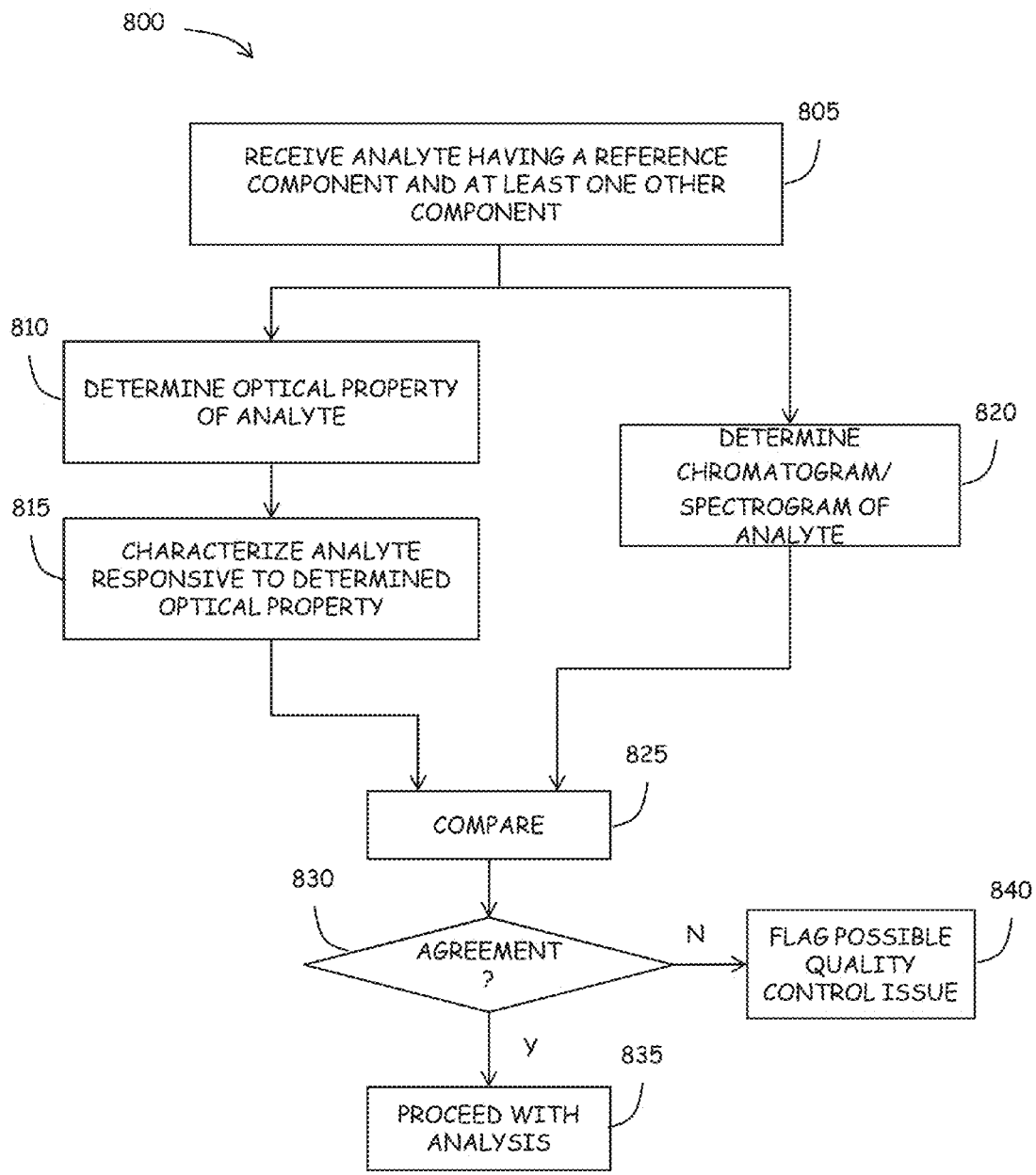
FIG. 9 shows a flow diagram of an embodiment of a process for quality control in which results of optical analysis and chromatography are compared.

Alternatively or in addition, such gas chromatography response forecasting can be used to evaluate of the quality of acquired data. FIG. 9 shows a flow diagram of an embodiment of a process 800 for quality control in which results of optical analysis and chromatography are compared.

A fluid sample having a reference component and at least one other component is received at 805. An optical property of the sample is determined at 810. The sample is characterized at 815 responsive to determined optical property. A chromatogram of sample is determined at 820. Results obtained from the optical analyzer and from the chromatograph are compared at 825 for the sample. If there is sufficient agreement at 830, for example within some predetermined tolerance, analysis of the fluid sample proceeds at 835 according to any of the techniques described herein. Otherwise, a possible quality control issue is identified or otherwise flagged at 840.

In other embodiments, methodologies such as those described herein can be applied to quantify a target component of a fluid sample using other analytical methods of formation fluid analysis. Such alternative analytical methods include mass spectrometry, ion mobility spectrometry, liquid chromatography, super critical liquid chromatography.

The term "live fluid" such as live oil is commonly used to refer to pressurized reservoir fluid samples that remain in single phase. Additionally, for the purpose of clarity, the term "analyte" is hearing used to refer to a fluid sample that is undergoing analysis. In accordance with the present invention, the analyte may be single phase or multiphase and may include a liquid hydrocarbon phase, a water phase, or a gaseous hydrocarbon phase.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention.

While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects.

Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

We claim:

1. A fluid analyzer for evaluating a fluid sample, the fluid analyzer comprising:
    an optical analyzer adapted to receive at least a portion the fluid sample, the optical analyzer configured to determine an optical property of the fluid sample and to provide an optical analyzer output signal indicative of the determined optical property;
    a composition analyzer adapted to receive at least a portion of the fluid sample, the composition analyzer configured to determine a component composition of the fluid sample and to provide a composition analyzer output signal indicative of the determined component composition; and
    a data processor in communication with each of the optical analyzer and the composition analyzer, the data processor configured to determine a quantity of a target component within the fluid sample using (i) a quantity of a reference component within the fluid sample obtained from the optical analyzer output signal, (ii) a response area of the reference component obtained from the composition analyzer output signal, and (iii) a response area of the target component obtained from the composition analyzer output signal.

2. The fluid analyzer of claim 1, wherein the data processor is configured to determine the quantity of the target component ($W_i^{GC}$) according to:

$$W_i^{GC}(\%) = \frac{A_i^{GC} \times R_i^{GC} \times W_{Ref}^{IFA}}{A_{Ref}^{GC} \times R_{Ref}^{GC}}$$

where: $W_i^{GC}$=the quantity of the target component;
$A_i^{GC}$=the response area of the target component obtained from the composition analyzer output signal;
$A_{ref}^{GC}$=the response area of the reference component obtained from the composition analyzer output signal;
$W_{ref}^{IFA}$=the quantity of the reference component determined from the optical analyzer output signal;
$R_i^{GC}$=a composition analyzer detector response factor for the target component; and
$R_{ref}^{GC}$=a composition analyzer detector response factor for the reference component.

3. The fluid analyzer of claim 1, wherein the optical analyzer comprises an optical absorption spectrometer.

4. The fluid analyzer of claim 1, wherein the composition analyzer comprises a gas chromatograph.

5. The fluid analyzer of claim 1, wherein the composition analyzer is configurable based on the optical analyzer output signal.

6. The fluid analyzer of claim 1, wherein each of the optical analyzer and composition analyzer is adapted for use downhole, within a wellbore, such that the fluid sample is obtainable in situ.

7. The fluid analyzer of claim 1, further comprising a multiphase flowmeter adapted to receive at least a portion the fluid sample outside of a wellbore producing the fluid sample, at least one of the optical analyzer and composition analyzer receiving the fluid sample from the multiphase flowmeter.

8. The fluid analyzer of claim 1, wherein the fluid sample comprises hydrocarbons.

9. A method for analyzing a fluid, comprising:
    receiving a fluid sample;
    determining an optical property of the fluid sample using optical analysis;
    determining a quantity of a reference component within the fluid sample using the optical property;
    determining a component composition of the fluid sample using gas chromatographic analysis, wherein the determining the component composition comprises: (i) generating a chromatogram of the fluid sample, (ii) determining a response area for a target component in the chromatogram, and (iii) determining a response area for the reference component in the chromatogram; and determining a quantity of target component using the component composition of the fluid sample and the quantity of the reference component.

10. The method of claim 9, wherein determining the optical property of the fluid sample comprises subjecting the fluid sample to optical absorption spectrometry.

11. The method of claim 9, wherein quantifying the target component comprises evaluation of the algorithm:

$$W_i^{GC}(\%) = \frac{A_i^{GC} \times R_i^{GC} \times W_{Ref}^{IFA}}{A_{Ref}^{GC} \times R_{Ref}^{GC}}$$

where: $W_i^{GC}$=the quantity of target component;
$A_i^{GC}$=the response area of the target component from the chromatogram;
$A_{ref}^{GC}$=the response area of the reference component from the chromatogram;
$W_{ref}^{IFA}$=the quantity of reference component;
$R_i^{GC}$=a gas chromatography response factor for the target component; and
$R_{ref}^{GC}$=a gas chromatography response factor for the reference component.

12. The method of claim 9, further comprising deriving from the determined optical property, one or more other properties selected from the group consisting of: weight percentage of $CH_4$ component, weight percentage of $C_2H_6$—$C_5H_{12}$ components, collectively; weight percentage of $C_6$+, collectively; formation pressure; formation temperature; gas-oil ratio; and condensate-gas ratio.

13. The method of claim 9, wherein the acts of receiving a fluid sample, determining an optical property, and determining the component composition are accomplished downhole, within a wellbore.

14. The method of claim 9, further comprising:
passing the fluid sample through a multiphase flowmeter, wherein the method is performed outside of a wellbore producing the fluid sample.

15. The method of claim 9, further comprising:
pre-configuring a gas chromatograph based on the determined optical property of the fluid sample, wherein the gas chromatograph is adapted for determining the component composition of the fluid sample.

16. The method of claim 9, further comprising:
comparing the determined optical property with the determined component composition, wherein an unfavorable comparison is indicative of a lack of quality in at least one of (1) the determination of the optical property or (2) the determination of the component composition.

17. The method of claim 9, further comprising:
repeating the act of determining the quantity of the target component for other target components within the fluid sample; and
generating a summary report indicative of the quantities of target components.

18. A method for analyzing a fluid, the method comprising:
receiving a fluid sample;
determining an optical property of the fluid sample using optical analysis;
determining a quantity of a reference component within the fluid sample using the optical property;
determining a component composition of the fluid sample using gas chromatographic analysis; and
determining a quantity of target component using the component composition of the fluid sample and the quantity of the reference component,
wherein the act of determining the quantity of the target component comprises determining at least one of (1) weight fraction, (2) weight percentage, (3) mole fraction, or (4) mole percentage.

* * * * *